(12) United States Patent
Vincent

(10) Patent No.: US 10,076,553 B2
(45) Date of Patent: Sep. 18, 2018

(54) DIETARY PRODUCT INTENDED FOR THE PREVENTION OF CARDIOMETABOLIC RISK

(71) Applicant: INTERNATIONAL NUTRITION RESEARCH COMPANY, Luxembourg (LU)

(72) Inventor: Claude Vincent, Bordeaux (FR)

(73) Assignee: INTERNATIONAL NUTRITION RESEARCH COMPANY, Luxembourg (LU)

( * ) Notice: Subject to any disclaimer, the term of this patent is extended or adjusted under 35 U.S.C. 154(b) by 89 days.

(21) Appl. No.: 14/353,541

(22) PCT Filed: Oct. 25, 2012

(86) PCT No.: PCT/EP2012/071113
§ 371 (c)(1),
(2) Date: Apr. 23, 2014

(87) PCT Pub. No.: WO2013/060758
PCT Pub. Date: May 2, 2013

(65) Prior Publication Data
US 2014/0287057 A1 Sep. 25, 2014

(30) Foreign Application Priority Data

Oct. 25, 2011 (FR) ..................................... 11 59663

(51) Int. Cl.
| | |
|---|---|
| *A61K 38/17* | (2006.01) |
| *A61K 38/01* | (2006.01) |
| *A61K 35/20* | (2006.01) |
| *A61K 33/30* | (2006.01) |
| *A61K 31/145* | (2006.01) |
| *A61K 31/198* | (2006.01) |
| *A61K 31/201* | (2006.01) |
| *A61K 31/202* | (2006.01) |
| *A61K 31/405* | (2006.01) |
| *A61K 31/4415* | (2006.01) |
| *A61K 31/519* | (2006.01) |
| *A61K 31/59* | (2006.01) |
| *A61K 33/06* | (2006.01) |
| *A61K 33/24* | (2006.01) |
| *A23L 33/18* | (2016.01) |
| *A23L 33/19* | (2016.01) |

(52) U.S. Cl.
CPC .......... *A61K 38/1709* (2013.01); *A23L 33/18* (2016.08); *A23L 33/19* (2016.08); *A61K 31/145* (2013.01); *A61K 31/198* (2013.01); *A61K 31/201* (2013.01); *A61K 31/202* (2013.01); *A61K 31/405* (2013.01); *A61K 31/4415* (2013.01); *A61K 31/519* (2013.01); *A61K 31/59* (2013.01); *A61K 33/06* (2013.01); *A61K 33/24* (2013.01); *A61K 33/30* (2013.01); *A61K 35/20* (2013.01); *A61K 38/018* (2013.01)

(58) Field of Classification Search
None
See application file for complete search history.

(56) References Cited

U.S. PATENT DOCUMENTS 7,618,648 B2 * 11/2009 Gerhardt ................. A23L 1/296
424/439
2007/0166411 A1 * 7/2007 Anthony ................. A23L 1/296
424/750
2009/0181145 A1 7/2009 Pandey et al.

FOREIGN PATENT DOCUMENTS

| EP | 2 149 369 A1 | 2/2010 |
|---|---|---|
| FR | 2 902 607 A1 | 12/2007 |
| WO | 2004/014152 A1 | 2/2004 |
| WO | 2007/022312 A2 | 2/2007 |
| WO | 2009/115331 A2 | 9/2009 |
| WO | 2010/043415 A2 | 4/2010 |
| WO | 2010/047581 A1 | 4/2010 |
| WO | 2010/114627 A1 | 10/2010 |

OTHER PUBLICATIONS

International Search Report dated Jan. 10, 2013, corresponding to PCT/EP2012/071113.
Lourenco Da Costa et al.: "Effect of heat and enzymatic treatment on the antihypertensive activity of whey protein hydrolysates", International Dairy Journal, Elsevier Applied Science, Barking, GB, vol. 17, No. 6, Feb. 20, 2007 (Feb. 20, 2007), pp. 632-640.

* cited by examiner

*Primary Examiner* — Amy Lynn Clark
(74) *Attorney, Agent, or Firm* — Young & Thompson

(57) ABSTRACT

A dietary product for preventing cardiometabolic risk in humans, in particular for reducing visceral fat and deep subcutaneous fat, includes in particular a mixture of: a whey hydrolysate having a molecular weight of between 200 and 10,000 daltons, an isolate and/or concentrate of whey, and calcium caseinate.

14 Claims, No Drawings

DIETARY PRODUCT INTENDED FOR THE PREVENTION OF CARDIOMETABOLIC RISK

This invention relates to a dietary product and its use in particular for the prevention of cardiometabolic risk.

Cardiometabolic risk refers to the presence in an individual of several clinical and biological signs that increase the risk of heart disease, cardiovascular accidents, and type 2 diabetes, without, however, these signs necessarily being perceived by the individuals who are affected.

The primary signs of risk of metabolic and cardiovascular anomalies are a large abdominal perimeter and a high level of triglycerides in the blood. They are associated with at least one other risk factor, such as arterial hypertension, high blood sugar, a reduced HDL level, etc.

The cardiometabolic risk is correlated to overweight and in most cases to a poor lifestyle. Nevertheless, any overweight, even obesity, does not necessarily pose vital risks to health. It is the location of the adipose deposits that have an impact on whether risks of metabolic anomalies arise. Actually, for several years, it has been noted that cardiometabolic problems have been linked to visceral fat, i.e., the deep fat around the waistline. In addition, recent research has demonstrated that deep subcutaneous fat had the same physiopathological effect as visceral fat. In the two cases, the size of the visceral adipocyte and the number of macrophages have significance in cardiometabolic risk.

By contrast, the subcutaneous fat of the first two layers, although it is unsightly, does not in itself pose a health problem.

The visceral fat and the fat of the deep subcutaneous layer, containing very active macrophages from a hormonal standpoint, bring about impairments of the liver, the pancreas, and the energy-regulating system at the brain and the intestine, as well as numerous deficiencies caused by minor and chronic inflammation of the body. This chronic inflammation is responsible for the formation of fat plaque in the vessels, which is deposited on the walls (angina pectoris and arteritis of the lower limbs), and ends up rupturing (heart attack and vasculocerebral accident) owing to the action of one of the adipocytokines of the inflammation of the CRP ("C Reactive Protein"). In addition, because of the formation of their waste, free radicals hamper the exchanges at the level of the cells, causing intolerance to glucose, insulin resistance, and then diabetes.

To prevent cardiometabolic risk, it is therefore important to be able to act on the visceral fat and on the deep subcutaneous adipose tissue.

Currently, the existing solutions for preventing cardiometabolic risk are limited.

None of the regimens proposed since the appearance of cardiometabolic risk in the 1980s, be they balanced, hyperproteinated, hyperglucidic, hyperlipidic, very restrictive or unbalanced, has solved the specific problems of deficiencies and pathological particularities of this syndrome. High-protein diets even aggravate metabolic deficiencies.

Furthermore, the proposed medications act on a consequence of the metabolic syndrome, such as hyperglycemia, hypertension, hypertriglyceridemia, or hypercholesterolemia, but not on the entire metabolic syndrome.

It is known that the loss of deep subcutaneous and visceral fat is the sole possibility for cancelling out the action of macrophages of the adipose tissue by the reduction in the size of the adipocytes through their lipolysis without, however, understanding the relationship between these two actions for regulation of inflammation, lipolysis of adipocytes, and regulation of the signal of the NF-kappa B inflammation of the macrophages. Clinically, it is demonstrated that the NF-kappa B signal of the macrophages of the adipose tissue undergoes the reduction in the size of the adipocyte. Starting at 5% and definitely at 10% loss in the circumference of the waistline, the cardiometabolic risk factors are normalized.

Under a hyper-restrictive regimen (less than 800 kcal/day), the loss of visceral fat and lean body mass is significant but often aggravates the components of the metabolic syndrome owing to the rebound effects of regaining weight. In addition, the loss of subcutaneous fat is achieved only with difficulty, often at the end of the regimen if it is very restrictive and very long.

There is therefore a need for an effective, natural, and easy-to-use solution, which is capable of reducing visceral fat and deep subcutaneous fat by preventing cardiometabolic risk.

To respond to this, this invention proposes using a particular composition comprising a mixture of active ingredients consisting of at least:
  A whey hydrolyzate with a molecular weight of between 200 and 10,000 daltons,
  An isolate and/or a concentrate of whey, and
  Calcium caseinate.

Advantageously, such a composition can be used as a dietary product that is intended in particular for the prevention of cardiometabolic risk. The composition according to the invention can be used in particular for reducing deep subcutaneous and visceral fat for prevention of cardiometabolic risk.

The invention is now described in detail.

The purpose of the invention is therefore a dietary composition that is intended for the prevention of cardiometabolic risk, comprising a mixture of active ingredients that consists of at least:
  A whey hydrolyzate with a molecular weight of between 200 and 10,000 daltons,
  An isolate and/or a concentrate of whey, and
  Calcium caseinate.

In terms of the invention, dietary composition or dietary product is defined as a product that is intended for a particular diet, in addition to a restrictive regimen and/or a balanced diet. The dietary composition or the dietary product according to the invention is particularly suited to individuals who wish to lose visceral fat and subcutaneous fat or simply weight, either for medical reasons for primary or secondary prevention of cardiometabolic diseases, or for aesthetic reasons.

In terms of the invention, whey hydrolyzate is defined as any molecule or mixture of molecules obtained by a process that comprises a stage for chemical hydrolysis or enzymatic hydrolysis of whey.

In terms of the invention, whey isolate is defined as a whey extract that contains less than 1% lactose and fats.

In terms of the invention, whey concentrate is defined as a whey extract that is obtained by concentration of whey.

The whey hydrolyzate has a molecular weight of between 200 and 10,000 daltons, preferably between 200 and 3,500 daltons. It essentially consists of dipeptides and tripeptides.

In a preferred way, it involves a peptide hydrolyzate of whey comprising at least 90% peptides by weight of dry material of the hydrolyzate.

The isolate and/or the concentrate of whey preferably has/have a molecular weight of between 15,000 and 20,000 daltons.

The whey isolate is preferably produced from fresh milk and/or from whey from dairies that do not pasteurize the milk to prevent the destruction of beta-lactoglobulin and alpha-lactalbumin and that extract the whey by ultrafiltering or microfiltering (size of the filters of 0.1 μm). The isolate that is obtained by ion exchange is less suitable because of its low content of beta-lactoglobulin and alpha-lactalbumin. The isolate contains less than 1% lactose and fats, and its peptide concentration is preferably at least 90% by weight of dry material.

The whey concentrate is preferably obtained from an unpasteurized dairy whey, containing beta-lactoglobulin, alpha-lactalbumin, and glycomacropeptides. The concentration of peptides of the concentrate is preferably at least 80% by weight of dry material.

Furthermore, the calcium caseinate used in the composition according to the invention preferably has a molecular weight of between 20,000 and 35,000 daltons.

Advantageously, the different components of the composition act in synergy. The presence of the particular hydrolyzate associated with that of the isolate and/or the concentrate of whey makes it possible in particular to accelerate the loss of visceral fat and the loss of deep subcutaneous fat and manipulates the feeling of fullness. Calcium caseinate in particular has a lasting appetite-suppressant effect.

In a preferred way, the ratio by weight between the calcium caseinate and the mixture that consists of the hydrolyzate and the isolate and/or the concentrate of whey is between 0.8 and 1.2 in the composition. Such a characteristic also promotes the loss of visceral fat and deep subcutaneous fat.

According to a particularly suitable embodiment, the mixture of active ingredients of the composition also comprises a mixture of amino acids. The presence of amino acids makes it possible to improve the effectiveness of the dietary composition according to the invention.

The amino acids that are present in the composition are preferably at least tryptophan, glutamine, leucine, arginine and/or taurine, but the composition can contain other amino acids, such as isoleucine, valine, phenylalanine or tyrosine. Very preferably, the composition according to the invention comprises at least tryptophan, leucine, arginine, and taurine.

When tryptophan is present, it should represent between 6 and 9%, preferably approximately 7%, by weight of neutral amino acids that are present in the composition (leucine, isoleucine, valine, phenylalanine, tyrosine, and tryptophan). This particular proportion makes it possible to ensure that a suitable quantity of tryptophan can pass through the hematoencephalic barrier to be transformed into serotonin in such a way in particular as to affect the feeling of fullness in addition to the actions of calcium caseinate, arginine, and taurine coupled to zinc for the intestinal hormones, in particular CCK and GLP1, and to promote stress management.

When arginine and taurine are present, the ratio of the weight of arginine to the weight of taurine is between 1.5 and 2.

In addition to the mixture of hydrolyzate, isolate and/or concentrate of whey and calcium caseinate, and amino acids, the mixture of active ingredients of the composition according to the invention can comprise one or more of the elements that are selected from among milk calcium, magnesium, vitamin B6, vitamin B9, vitamin E, vitamin D, zinc, and chromium.

Likewise, the composition can contain essential fatty acids, in particular omega-3 fatty acids. These are preferably omega-3 fatty acids of plant origin, with a high proportion of EPA.

The different components of the composition according to the invention act in synergy for obtaining surprising effects that are particularly suitable for the prevention of cardio-metabolic risk.

According to a variant, the composition can also contain additional components that are known for improving the adaptation to stress and for regulating the secretion of ACTH and cortisol, such as, for example, the rosavin that is extracted from rhodiola and/or ginsenoside that is extracted from panax ginseng and/or the eugenol that is extracted from ocimum sanctum and/or the icariin that is extracted from epimedium and/or the phosphatidyl serine and/or phytosterol esters.

According to a preferred embodiment, the mixture of active ingredients of the composition according to the invention comprises at least:

8 to 12% whey hydrolyzate, 15 to 20% isolate and/or concentrate of whey, 20 to 25% calcium caseinate, with the percentages being given by weight of dry material of all of the active ingredients that are present in the composition (apart from the possible vehicles). The composition can also contain elements that are added freely, such as amino acids, vitamins, and minerals, which are added to the native components of the whey hydrolyzate, the whey isolate, the whey concentrate, and calcium caseinate.

The composition according to the invention preferably consists of at least:

1.5 to 3% tryptophan, 12 to 20% branched amino acids, 6 to 10% aromatic amino acids, 0.8 to 1.5% taurine, 1.6 to 3% arginine, 1.2 to 3% milk calcium, 0.5 to 1% magnesium, 0.4 to 1% omega-3 fatty acids, 1 to 2 mg of vitamin B6 per 50 g of the composition without vehicles, 5 to 15 mg of zinc per 50 g of composition without vehicles, 1 to 3 μg of vitamin D per 50 g of composition without vehicles, 75 to 150 μg of chromium per 50 g of composition without vehicles, 100 μg of vitamin B9 per 50 g of composition without vehicles, 10 mg of vitamin E per 50 g of composition without vehicles, with the percentages being given by weight of dry material of all of the active ingredients that are present in the composition (apart from the possible vehicles), a portion of the components coming from the whey hydrolyzate, the whey isolate, the whey concentrate, and calcium caseinate, and the remainder being freely added in the form of amino acids, vitamins and minerals.

The branched amino acids of the composition consist of leucine, isoleucine, and valine, preferably:
- 50 to 60% leucine,
- 18 to 25% isoleucine, and
- 20 to 28% valine, and the aromatic amino acids of tryptophan, phenylalanine, and tyrosine, preferably:
- 15 to 24% tryptophan,
- 38 to 46% phenylalanine, and
- 35 to 43% tyrosine.

The composition according to the invention can be obtained by a process as described below:
- A first mixture is obtained by mixing components in the following order: calcium caseinate, whey isolate, whey concentrate, whey hydrolyzate, free amino acids, magnesium, and milk calcium. The pH is to be around 7 and is stabilized at this level.
- Addition to the first mixture of vitamins, minerals, and fatty acids.
- A powder that can be transformed into a tablet or liquid, or else used in its powder form in packets, sticks, containers, or capsules, for example, is thus obtained.

The composition according to the invention, when it is administered by oral means in sufficient quantity, makes it possible to affect directly the loss of deep subcutaneous and visceral fat, in particular owing to the presence of the mixture of hydrolyzate and isolate and/or concentrate of whey.

It also acts as an appetite suppressant and ensures a feeling of fullness, in particular by the action of whey hydrolyzate. This effect is enhanced in the presence of tryptophan and can even be accentuated owing to the presence of other components, in particular milk calcium, histidine, vitamin B6 and/or magnesium, with the various components then acting in synergy.

The composition according to the invention makes it possible to lose weight permanently in particular by the supply of tryptophan that regulates fullness in synergy with the action on the inflammation of taurine, arginine, zinc, and chromium by a regulation of the NF-kappa B signal of the macrophages of adipocytokines and regulation of incretin hormones, in particular CCK and GLP1. In addition, it reduces the circumference of the waistline, while maintaining the lean body mass, in particular by the supply of branched amino acids.

According to another advantage, the composition is also capable of affecting numerous other factors of cardiometabolic risk. In particular, it is capable of reducing stress, normalizing arterial tension, limiting oxidation, reducing ultrasensitive CRP inflammation, limiting coagulation, regulating cholesterol and triglycerides, and/or reducing blood sugar and/or postprandial blood sugar.

The object of the invention is therefore the composition as described above for its use as a dietary product or for the preparation of an orally-administered dietary product for the prevention of cardiometabolic risk in humans.

The composition according to the invention can come in any form that is suitable for administration by oral means. It can come in particular in the form of powder or granules, ready-to-use drinks, bars or logs, with conventional vehicles and additional ingredients that are known to one skilled in the art being added to the composition.

Preferably, it comes in the form of powder or granules packaged in a packet to be diluted in water.

The daily dose of composition according to the invention (dose of a mixture of active ingredients without vehicles) is preferably between 66 and 110 g, preferably in two servings of 33 to 55 g, one taken in the morning at breakfast or at 1100 hours with a snack, and one with a snack in the afternoon.

Advantageously, the bioavailability in the body of amino acids, peptides and proteins that are present in the composition is between 10 minutes and 5 hours, which makes possible an action that is both rapid and that continues over time in such a way as to limit the quantity of food to be taken daily.

In addition, the presence of milk calcium makes it possible to enhance the palatability of the dietary product according to the invention by masking in particular the bitter taste of the whey hydrolyzate in such a way that it takes part in eliminating the risk that the individuals stop consuming it for reasons of taste and abandon their regimen before its end.

The dietary composition makes it possible to reduce the visceral fat and the deep subcutaneous fat in overweight individuals, in particular by the acceleration of the lipolysis process, the regulation of the oxidation-inflammation-coagulation triad, and the supply of active ingredients compensating for the pathological deficiencies of overweight individuals and primarily individuals with abdominal obesity.

The combination of fatty acids, in particular omega-3 fatty acids, with milk calcium and the particular amino acid mixture according to the invention also makes it possible to retard the transformation of pre-adipocytes into visceral adipocytes.

The invention also makes it possible:
- To prevent the formation and the breaking of atheroma plaque in particular by significantly reducing the secretion of inflammatory adipocytokines in such a way as to prevent cardiovascular accidents,
- To limit the risk of diabetes, in particular by restoring the elasticity of the cellular membrane, which facilitates the exchanges of glucose and cholesterol and improves the functioning of the receptors of leptin, insulin, and triglycerides, and
- To combat chronic stress both at the level of the adaptation of the individual to stress and the monitoring of cortisol.

The invention is now illustrated by a nonlimiting example of dietary composition, coming in the form of a powder of 55 g (active ingredients and vehicles) packaged in a packet.

This composition is obtained from the following active ingredients:
- 5 g of whey hydrolyzate with a molecular weight of between 200 and 3,500 daltons,
- 10 g of isolate and/or concentrate of whey with a molecular weight of between 15,000 and 20,000 daltons,
- 13 g of calcium caseinate with a molecular weight of between 20,000 and 35,000 daltons,
- 1 mg of vitamin B6,
- 10 mg of zinc,
- 0.45 g of taurine,
- 40 μg of chromium,
- 10 mg of vitamin E,
- 100 μg of vitamin B9,
- 2.5 μg of vitamin D,
- 270 mg of omega-3 fatty acids of plant origin,
- Enough to produce 4.2 g of leucine,
- Enough to produce 0.8 g of tryptophan,
- Enough to produce 0.9 g of arginine,
- Enough to produce 0.75 g of milk calcium, and
- Enough to produce 0.36 g of magnesium.

"Enough to produce Xg" of an element of the composition is defined as the total quantity of this element in the composition: quantity provided by the protides (calcium caseinate, whey isolate, whey concentrate, whey hydrolyzate) and completed by an addition of the element in free form for reaching Xg.

When such a therapy product is administered twice per day (one packet in the morning at breakfast or at 1100 hours with a snack and a packet with a snack in the afternoon) for at least 90 days, and preferably 180 days, to patients who exhibit signs associated with cardiometabolic risk, a reduction in the circumference of the waistline is noted that is characterized by a significant reduction in fat and in particular deep subcutaneous and visceral fat. The loss of body fat is usually more significant than the total weight loss, which involves a relative increase of the lean body mass. The composition according to the invention makes it possible in particular to reduce the visceral fat between 5 and 10% of the circumference of the waistline, with this reduction signifying a reduction in the risk of cardiometabolic diseases. It is reflected in particular by:

- A reduction in the T cholesterol level,
- A reduction in the LDL cholesterol level,
- A stabilization of the drop in the HDL cholesterol level or a slight rise,
- A reduction in fasting blood sugar in patients with insulin resistance or glucose intolerance and HbA1c in patients suffering from type II diabetes,
- A normalization of arterial tension, and
- A normalization of CRP us and fibrinogen.

The invention is now illustrated by a study whose primary objective is to show the effect of the composition on the reduction in the circumference of the waistline and on other factors with cardiometabolic risk.

The study was done on patients:

Having an excessive waistline circumference relative to the IDF 2006 standards (80 cm for women and 94 cm for men), Having at least two cardiometabolic risk factors selected from among: high arterial pressure, high blood sugar, dyslipidemia (high triglycerides, high LDL cholesterol, and high total cholesterol, low HDL), smoking, and family medical history.

The patients followed a regimen adapted to their dietary habits, balanced (50% carbohydrates, 35% lipids, 15% proteins; carbohydrates with a glycemic load of less than 10), hypocaloric (restriction of 700 kcal on the calculated Total Energy Expenditure [TEE]) and comprising two servings per day of a composition according to the invention (that of the example) providing 360 kcal taken into account in the daily ration. A physical activity with a minimum of 5,000 steps (measured with a pedometer) was prescribed. This intensive phase should be stopped when a reduction of 10% of the waistline circumference was reached or when the latter returned to the IDF standards. It should be interrupted at the end of 9 months if the objective was not reached.

This intensive phase should be followed by a stabilization phase comprising a balanced diet without caloric restriction with one dose of composition according to the invention (that of the example) per day.

92 patients were included in the initial study: contact was lost with 28 of them after the inclusion, 64 completed the intensive nutritional intervention phase, and 34 participated in the stabilization phase.

The basic data of the 64 patients who were included and who completed the intensive nutritional phase of the study are presented in the following table:

TABLE 1

| | Patients Having Completed the Nutritional Intervention Phase (Mean ± Standard Deviation or Number of Patients) N = 64 | |
| --- | --- | --- |
| | Men 15 | Women 49 |
| Mean Age (Years) | 53.7 ± 11.1 | 53.0 ± 11.0 |
| Waistline Circumference (cm) | 101.9 ± 7.3 | 91.9 ± 10.2 |
| Waistline (cm) | 177.8 ± 4.9 | 163.6 ± 6.1 |
| Initial Weight (kg) | 92.3 ± 8.6 | 74.3 ± 11.5 |
| BMI (kg/m$^2$) | 29.2 ± 2.6 | 27.8 ± 4.9 |
| Inclusion of Waistline Circumferences Outside the Norms with | | |
| BMI < 25 | 0 | 13 |
| With BMI > 25 | 36 | 15 |
| Including the Obese (BMI > 30) | 4 | 11 |
| REE Basic Metabolism (Kcal) | 1,745 ± 272 | 1,367 ± 110 |

The results that are obtained for the 64 patients who completed the intensive nutritional phase are presented in the table below:

TABLE 2

| | Initial Value (Mean ± Standard Deviation) | Final Value | Evolution (Mean ± Standard Deviation) | % Evolution |
| --- | --- | --- | --- | --- |
| REE (Kcal) | 1,455 ± 227 | 1,439.5 ± 201.5 | −15.8 ± 117 | −0.6 |
| Waistline Circumference (cm) | 94.2 ± 10.5 | 85.0 ± 7.5 | −9.2 ± 6.8 | −9.4 |
| Weight (kg) | 78.5 ± 13.3 | 69.3 ± 10.6 | −9.2 ± 5.3 | −11.4 |
| BMI | 28.2 ± 4.5 | 24.8 ± 3.0 | −3.3 ± 2.1 | −11.4 |
| Body Fat (kg) | 27.6 ± 7.4 | 20.0 ± 4.9 | −7.5 ± 6.2 | −25.8 |
| Lean Body Mass (kg) | 50.9 ± 10.0 | 49.3 ± 9.9 | −1.6 ± 3.2 | −3.1 |
| Systolic Arterial Tension (mm of Hg) | 128 ± 15.8 | 117.6 ± 12.1 | −10.5 ± 14.1 | −7.4 |
| Diastolic Arterial Tension (mm of Hg) | 80.2 ± 10.8 | 70.0 ± 6.1 | −10.3 ± 9.7 | −11.7 |
| Total Cholesterol (mmol/l) | 5.7 ± 1.0 | 5.1 ± 0.7 | −0.6 ± 0.6 | −9.4 |
| HDL (mmol/l) | 1.5 ± 0.5 | 1.5 ± 0.4 | 0 ± 0.1 | 0.7 |
| LDL (mmol/l) | 3.6 ± 0.9 | 3.3 ± 0.8 | −0.3 ± 0.5 | −7.9 |
| CT/HDL | 4.2 ± 2.4 | 3.6 ± 1.8 | −0.5 ± 0.8 | −9.4 |
| Triglycerides (mmol/l) | 1.2 ± 1.0 | 1.0 ± 0.3 | −0.2 ± 0.8 | −7.5 |
| Blood Sugar (mmol/l) | 5.8 ± 2.8 | 5.1 ± 0.4 | −0.7 ± 2.7 | −4.8 |
| Insulinemia (μU/ml) | 10.5 ± 6.9 | 7.0 ± 4.6 | −3.5 ± 3.1 | −30.1 |

TABLE 2-continued

| | Initial Value (Mean ± Standard Deviation) | Final Value | Evolution (Mean ± Standard Deviation) | % Evolution |
|---|---|---|---|---|
| HOMA-IR | 3.2 ± 3.8 | 1.6 ± 1.1 | −1.6 ± 3.2 | −35 |
| CRP us (mg/l) | 2.3 ± 3.1 | 1.4 ± 1.6 | −0.9 ± 2.1 | −17.8 |
| Fibrinogen (g/l) | 3.6 ± 0.8 | 3.2 ± 0.6 | −0.5 ± 0.5 | −11.5 |
| Creatinine (mg/l) | 7.8 ± 1.8 | 7.6 ± 1.2 | −0.2 ± 1.2 | / |
| Urea (g/l) | 0.4 ± 0.1 | 0.4 ± 0.4 | 0 ± 0.4 | / |

These results show a mean loss of nearly 10% of the waistline circumference in less than 9 months.

In addition, the composition according to the invention makes possible a significant reduction in other cardiometabolic risk factors, in particular:

Loss of weight: the weight loss is of the same order as the loss of waistline circumference, or 9.2 kg. The number of patients with BMI<25 went from 13 to 41 inclusive at the end of the study. The loss of body fat relative to the lean body mass predominated, bringing the ratio of the lean body mass to the total weight from 65% to 71%.

Arterial pressure: arterial pressure is improved. It was normalized in all 17 patients suffering from hypertension, inclusive.

Biological parameters: the biological parameters have been improved, in particular:

The lipid profile: 11 patients out of 19 normalized their LDL at the end of the weight loss phase Inflammation markers: 10 patients who had a high CPR us normalized it as well as 4 patients for fibrinogen, which is unusual Insulin resistance markers: 10 patients for blood sugar and 4 patients for insulinemia who were outside the norms regulated the risk of diabetes; in addition, for all of the subjects, a drop of 35% in insulin resistance characterized by HOMA-IR3 was noted Creatinine was lowered, and urea remained stable, which suggests that the nutritional protocol used in the study does not have a detectable impact on renal function.

Furthermore, advantageously, in 6 months, no undesirable effect was reported spontaneously.

The invention claimed is:

1. A method for reducing cardiometabolic risk in humans who exhibit signs associated with cardiometabolic risk, comprising orally administering to a human subject in need thereof a composition comprising effective amounts of whey hydrolysate having a molecular weight of between 200 and 10,000 daltons; an isolate and/or a concentrate of whey having a molecular weight of between 15,000 to 20,000 daltons; and calcium caseinate, as active ingredients; and wherein the composition further comprises, by weight of dry material of all active ingredients present in the composition, at least:

1.5 to 3% tryptophan;
12 to 20% branched amino acids, wherein said branched amino acids comprise leucine;
6 to 10% aromatic amino acids;
0.8 to 1.5% taurine;
1.6 to 3% arginine;
1.2 to 3% milk calcium;
0.5 to 1% magnesium;
0.4 to 1% omega-3 fatty acids; and 1 to 2 mg of vitamin B6 per 50 g of the composition without vehicles;
5 to 15 mg of zinc per 50 g of the composition without vehicles;
1 to 3 μg of vitamin D per 50 g of the composition without vehicles;
75 to 150 μg of chromium per 50 g of the composition without vehicles;
100 μg of vitamin B9 per 50 g of the composition without vehicles; and
10 mg of vitamin E per 50 g of the composition without vehicles.

2. The method according to claim 1, wherein the composition further comprises glutamine.

3. The method according to claim 1, wherein the calcium caseinate has a molecular weight of between 20,000 and 35,000 daltons.

4. The method according to claim 1, wherein the whey hydrolysate has a molecular weight of between 200 and 3,500 daltons.

5. The method according to claim 1, wherein the ratio by weight between the calcium caseinate and the total combined amount of the whey hydrolysate and the isolate and/or concentrate of whey is between 0.8 and 1.2.

6. The method according to claim 1, wherein the ratio of the weight of arginine to the weight of taurine is between 1.5 and 2.

7. The method according to claim 1, wherein the composition comprises:

8% to 12% by weight of the whey hydrolysate;
15% and 20% by weight of the isolate and/or concentrate of whey; and
20% and 25% by weight of the calcium caseinate.

8. The method according to claim 1, wherein the composition is in the form of a powder, granules, a ready-to-use drink, or bars or logs.

9. The method according to claim 1, wherein the method further comprises at least one of reducing visceral fat and reducing deep subcutaneous fat in the subject.

10. The method according to claim 1, wherein said method further comprises at least one of reducing waistline circumference, reducing stress, normalizing arterial tension, limiting oxidation, reducing ultrasensitive CRP inflammation, limiting coagulation, regulating cholesterol and triglycerides, reducing blood sugar, reducing postprandial blood sugar, and combinations thereof, in the subject.

11. The method according to claim 1, wherein the composition is administered to the subject in an amount of between 66 g to 110 g of composition per day.

12. The method according to claim 1, wherein the composition is administered to the subject in two doses of between 33 g to 55 g of composition per day.

13. The method according to claim 1, wherein reducing cardiometabolic risk in the subject comprises at least one of:

a reduction in the T cholesterol level;
a reduction in the LDL cholesterol level;
a stabilization of the drop in the HDL cholesterol level or a slight rise;
a reduction in fasting blood sugar in patients with insulin resistance or glucose intolerance;
a reduction in HbA1c in patients suffering from type II diabetes;
a normalization of arterial tension;
a normalization of CRP; and
a normalization of fibrinogen.

14. The method according to claim 1, comprising administering a dietary product comprising the effective amount of said composition to the subject.

* * * * *